(12) United States Patent
Aberbach (10) Patent No.: US 11,751,855 B2
(45) Date of Patent: Sep. 12, 2023

(54) COLLECTING URINE SAMPLES AND DATA THEREOF

(71) Applicant: Varda Margalit Aberbach, Tel Aviv (IL)

(72) Inventor: Varda Margalit Aberbach, Tel Aviv (IL)

(*) Notice: Subject to any disclaimer, the term of this patent is extended or adjusted under 35 U.S.C. 154(b) by 346 days.

(21) Appl. No.: 16/904,665

(22) Filed: Jun. 18, 2020

(65) Prior Publication Data
US 2020/0397414 A1  Dec. 24, 2020

Related U.S. Application Data

(60) Provisional application No. 62/863,289, filed on Jun. 19, 2019.

(51) Int. Cl.
*A61B 10/00* (2006.01)
*G01N 1/20* (2006.01)

(52) U.S. Cl.
CPC ......... *A61B 10/007* (2013.01); *G01N 1/2035* (2013.01); *G01N 2001/2085* (2013.01)

(58) Field of Classification Search
CPC .............. A61B 10/007; G01N 1/2035; G01N 2001/2085; G01N 1/20; G01N 2001/2078
USPC ............ 436/164; 73/863.41, 863.51–863.53, 73/864.51, 864.52; 600/573, 574
See application file for complete search history.

(56) References Cited

U.S. PATENT DOCUMENTS

| | | |
|---|---|---|
| 4,557,274 A | 12/1985 | Cawood |
| 9,155,525 B2 | 10/2015 | Lipinsky |
| 2004/0241052 A1* | 12/2004 | House ............... A61B 10/007 422/400 |
| 2006/0184064 A1* | 8/2006 | Paasch ............... A61B 10/007 4/144.1 |
| 2014/0213934 A1* | 7/2014 | Ellis ................. A61B 10/0096 600/573 |

(Continued)

FOREIGN PATENT DOCUMENTS

| | | | |
|---|---|---|---|
| CN | 109561888 | * | 4/2019 |
| GB | 2162312 A | | 1/1986 |
| WO | 2014152626 A3 | | 9/2014 |

OTHER PUBLICATIONS

Nabavizadeh P, Ghadermarzi S, Fakhri M. A new method to make 24-hour urine collection more convenient: a validity study. International Journal of Nephrology. May 20, 2014;2014. http://dx.doi.org/10.1155/2014/718147.

*Primary Examiner* — Robert R Raevis
(74) *Attorney, Agent, or Firm* — Dr. Hanan Farber Patent Agent Ltd.

(57) ABSTRACT

A collector for collecting urine samples is placed inside a toilet with an extension lip placed on a toilet seat disposed on top of the toilet. Upon collecting urine inside the collector, a sample of urine is extracted from inside the collector. The collector may include a socket. The sealed container may be inserted into the socket to extract the sample of urine. A hollow sleeve may be disposed inside or outside the collector. Urine disposed inside the collector and inside the sleeve may attain the same fluid level responsive to a fluid passage between the collector and the sleeve at the bottom of the collector. The volume of urine extracted from the sleeve may be proportional to the urine collected inside the collector with a known proportionality constant.

12 Claims, 10 Drawing Sheets

(56) References Cited

U.S. PATENT DOCUMENTS

2014/0276214 A1* 9/2014 Lipinsky .............. A61B 10/007
600/573

* cited by examiner

COLLECTING URINE SAMPLES AND DATA THEREOF

CROSS-REFERENCE TO RELATED APPLICATION

This application claims the benefit of U.S. Provisional Application No. 62/863,289, filed, Jun. 19, 2019, the disclosure of which is incorporated herein by reference.

FIELD AND BACKGROUND

1. Technical Field

The present invention relates to medical diagnostics and particularly to a collector for fluid, particularly urine collection and acquisition of data therefrom.

2. Description of Related Art

Urine tests are used to monitor our health during our entire life. Urine monitoring is performed by healthcare organizations, enforcement agencies, sports organizations, research, etc. The most common urine tests are urinalysis, culture and urine collection over a 24 hour period. Samples of long urine collections, in which urine is collected over time periods e.g. 6 hours, 12 hours, 24 hours, 48 hours, are mainly used to measure volumes of various substances (such as protein) or to monitor body fluid balance. Tracking variations in urine substances (such as calcium) over long time periods, usually requires patient's hospitalization.

The scale of urine tests is constantly growing as, in addition to the above, urine tests are used to check adherence to prescribed medications, detect diseases such as cancer and they play an increasing role in home healthcare monitoring. Urine tests may be interpreted immediately or in laboratories. Immediate diagnostics are mainly performed by urine dipsticks. When reacting with urine, chemicals in the dipsticks' pads may change color. The colors are compared to a scale indicating status of the tested substance. Current urine sample collection methods for independent people (free from diapers or catheter) are tedious and unaesthetic. People may be required to target their urine flow into a small cup or test tube, then bring the urine cup or the test tube to a clinic. People may be embarrassed carrying the urine cup and try to cover or hide it. Some are asked to pour the urine into a test tube when vacuum test tubes are not used. Inconvenience only grows when a person needs to perform a long urine collection and collect all her/his urine during a long collection time period. Carrying a collection bottle. e.g. a jar with removable cap to work/studies/errands is embarrassing and unpleasant, and the person may choose to stay at home. In addition, the person is confronted with unpleasant smells, urine spilling, weight of collection bottle. Depending on the protocol used, after completing the long urine collection, the person may bring the bottle to a clinic or pour urine from the jar to a small urine cup or test tube, bring the cup or the test tube. In order to fill a small cup or a test tube, the collected urine in the bottle should be mixed. Holding the jar and shaking it in order to blend the urine is heavy, unpleasant and might result in spilled urine. Total urine volume collected in 24 hours may be 0.8-2.0 liter and in special cases up to four liters. Sometime the bottles used for long urine collection are small and more than one bottle is used. If the clinic requires the urine sample in a small cup or a test tube, the person may be requested to read and note the total urine volume in the bottles, shake them and pour urine to a small cup in a volume proportional to the volume in each bottle, an error prone process.

In order to provide a urine sample for a culture test, the initial urine flow is not collected. A person may be instructed to first urinate into the toilet, then stop urine flow, take a small cup and urinate into the cup. Naturally this instruction is challenging for children, elderly people, pregnant women, sick people, disabled people and caregivers.

Due to difficulties in urine collection processes, adherence level with urine tests is low. Adherence is especially low with the 24 hour urine collection. In addition, many samples are rejected due to flaws in the long collection method, such as improper collection, improper urine mixing, missing information on the total urine volume which is essential for calculating volumes of substances (such as protein) in the urine. Therefore, in order to increase adherence, there is a need for a urine collection device that allows the user to naturally urinate (not into a small cup), without having to stop during the urination, obtain the urine sample easily and esthetically, without pouring or smelling the collected urine, a method which allows tracking and acquiring urine related data and without having to stay at home during long urine collections. There is a need to ensure the quality of the urine samples in order to avoid medical mistreatment.

BRIEF SUMMARY

Various systems and methods are provided for collecting urine samples, according to various aspects of the present invention. A collector is placed inside a toilet with an extension lip placed on a toilet seat disposed on top of the toilet. Upon collecting urine inside the collector, a sample of urine is extracted from inside the collector. The collector may include a socket configured to receive a sealed container with a seal. The sealed container may be inserted into the socket to penetrate the seal by the socket prior to the extraction of the sample of urine into the sealed container. The collector may include multiple compartments. An initial urine flow may be separated from a subsequent urine flow. The sample of urine may be extracted only from a compartment including the subsequent urine flow. A hollow sleeve may be disposed inside or outside the collector. Urine disposed inside the collector and inside the sleeve may attain the same fluid level responsive to a fluid passage between the collector and the sleeve at the bottom of the collector. Upon collecting the urine sample, the fluid passage may be closed between the collector and the sleeve. The volume of urine contained in the sleeve is extracted. The volume of urine extracted from the sleeve may be proportional to the urine collected inside the collector with a known proportionality constant. Urine sample may be repeatedly collected and the volume of urine collected during a previously determined time period; may be extracted multiple instances from the sleeve. A volume of urine contained in the sleeve is transferred to a receptacle. Urine accumulated in the receptacle may be proportional to a total volume of urine collected during the previously determined time period with the known proportionality constant. The receptacle may include a sensor configured to measure a parameter of the urine accumulated in the receptacle. The receptacle may include a dipstick. The dipstick may be provided in the dipstick drawer. The dipstick drawer may be configured to stream a portion of the urine that enters the receptacle and into the dipstick drawer to immerse the dipstick. An image of the urine may be captured through a transparent face of the receptacle. A sensor may be provided in the receptacle.

The foregoing and/or other aspects will become apparent from the following detailed description when considered in conjunction with the accompanying drawing figures.

BRIEF DESCRIPTION OF THE DRAWINGS

The invention is herein described, by way of example only, with reference to the accompanying drawings, wherein:

FIGS. 1a to 2a. present top and side views of the collector shown in FIGS. 1-4 and collector attachment extension for fitting over a toilet seat, according to features of the present invention;

FIGS. 20-1, 20-2, 20-3 and FIG. 20-4 illustrate respectively a three dimensional view, top view, front view and side view of a dipstick drawer according to features of the present invention;

DETAILED DESCRIPTION

Reference will now be made in detail to embodiments of the present invention, examples of which are illustrated in the accompanying drawings, wherein like reference numerals refer to the like elements throughout. The embodiments are described below to explain the present invention by referring to the figures.

By way of introduction, a principal intention of the present invention is to improve urine testing for healthcare monitoring, enforcement, sports or the like. In addition to collection of the urine sample, different embodiments of the present invention enable tracking, collecting, data acquisition and data-based user guidance. Disclosed embodiments allow the user to easily and esthetically collect a urine sample for a urine test, e.g. urinalysis, culture, 24-hour urine collection, and either interpret immediately and/or subsequently in a laboratory. The user may easily and esthetically collect samples of fluids for diagnosis.

According to exemplary embodiments of the present invention, the system may include two parts: a collector for collecting urine samples and a smart receptacle into which urine samples are later stored and possibly analyzed. For a urine sample, for single and/or long urine collections, the present disclosure provides a small and esthetic product that can be easily placed in a bag. The user may attach the collector to a toilet seat, may urinate in a natural mode (either sitting or standing) and may extract the urine sample into a sealed container, e.g. an evacuated tube, a culture device. The user may provide the sealed container to healthcare, enforcement or sports unit for further immediate and/or subsequent laboratory testing. Alternatively, the user may transfer the urine sample from the tube into a "smart" receptacle, for temporary storage and accumulation of all urine samples during long, e.g. 24 hour urine collections.

This disclosure allows the user to run immediate diagnostics without having to pour, smell, dip-into urine and with no medical staff assistance. This disclosure allows the user to provide a sample for culture test, by urinating freely with no disturbance. The user is free from the need to stop urinating, taking a cup and then proceed urinating. According to features of the present invention the user is freed from the need to collect all the urine given throughout long collections. Instead, at each urination throughout the long collection, a small urine volume is collected, proportional to the urine volume given at each urination. The smart receptacle includes a special container into which the urine sample of each urination is collected. Once the long urine collection is complete, the receptacle holds a true representation of the entire urine given throughout the long collection. The user easily obtains a sealed test tube (or a similar container) holding the urine sample of the long collection for either immediate diagnostics and/or further lab tests. Data (user ID, time stamp, volume, various chemical and pathological elements, etc.) may be collected by either hardware (sensors+IoT tools) or software, by photo capturing the smart receptacle and utilizing tools such as image processing. Data is transmitted over the network to both the monitoring authority (healthcare or other) and the user. An application may enable tracking, detection and user guidance. This disclosure is directed to free the user from the necessity to manually pour the urine into a small cup, a jar, a tube (or the like) and seal it, from having to manually measure the urine volume or manually track and report urine sample related data. The user can easily carry both the collector/s and the sealed smart receptacle in a handbag or the like, enjoy regular undisturbed daily routine when performing a long urine collection. The user is both guided along the collection process, updated and advised on the urine test results. Medical staff work becomes more efficient due to a higher quality of the urine samples and are partially freed from a tedious task. Embodiments of the disclosure enable continuous tracking of variations in urine substances (such as calcium) during many hours, without having to hospitalize the patient but rather allow the patient to enjoy regular undisturbed daily routine. Objects of the disclosure include providing a collector that enables obtaining a tube (or a similar container) without handling urine (handling is: targeting, pouring, spilling, touching); providing a portable device to accumulate a fractional volume proportional to urination volume during a time period; providing a system to separate between initial urine and the rest without contaminating the sample; providing a device that allows immediate diagnostics without handling urine; providing a portable container to collect several tubes (or similar containers) and mark their order, therefore; offering a new approach of detecting variations in urine substances using sensors or image capturing of the smart receptacle for volume and an additional parameter of accumulated urine;

freeing the user from storing and carrying a closed bottle of urine during long collection time periods and instead storing a proportional urine samples in a portable, aesthetic and small receptacle which may be provided in a small portable bag with several folded/squeezed small collectors and a smart receptacle to allow mobility.

Embodiments of the present invention are directed to urine collection and tracking, however variations may be directed to collecting and analyzing fluid content such as human breast milk, animal milk and agricultural oriented fluids.

Referring now to the drawings, FIGS. 1-4 illustrate respectively a three dimensional isometric view, top view, front view and side views of a first embodiment of a collector 10, according to features of the present invention. Collector 10, may be configured for one-time use or reusable, made of either a disposable material, or made of a durable reusable material. Collector 10 may be of a material that may dissolve when triggered following a chemical reaction or with fluid such as water, but not only. Shape of a collector 10 may be a pyramid, a cone or geometrically undefined such as a sack. For explanatory purposes only, the figures depict collector 10 shape as a pyramid. Collector 10 bottom may be pre-designed as horizontally balanced or may achieve horizontal balance by the weight of fluid filling it. Collector 10 may hold up to 1.2 liter or larger if needed of fluid, e.g. urine. Collector 10 upper end may be open or covered by a material that either collects, absorbs or diffuses the urine in order to avoid fluid (urine or other) backsplashes. The cover is made of either a disposable, dissoluble or a durable material.

Figure 1:
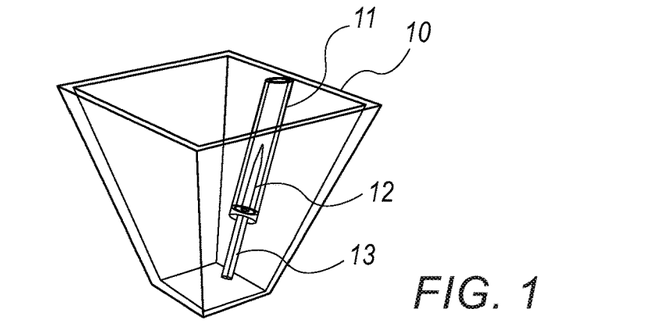
FIGS. 1 to 4 present respectively a three dimensional isometric view, top view, front view and side views of a first embodiment of a collector, according to features of the present invention.
Figure 1A:
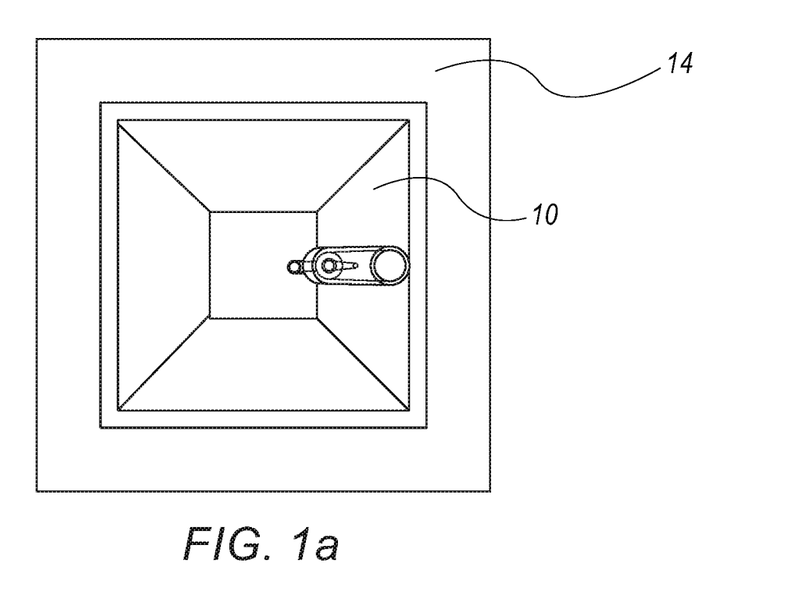
Figure 2:
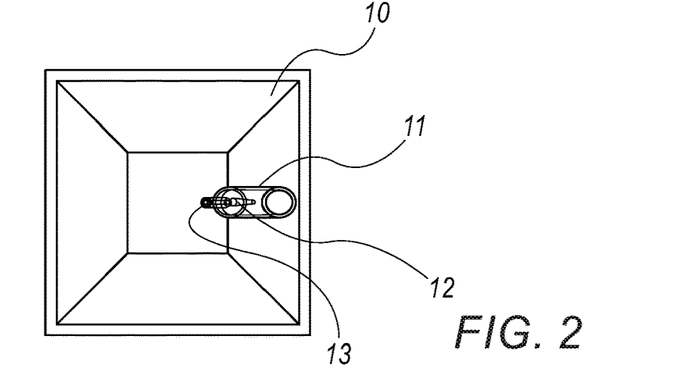
Figure 2A:
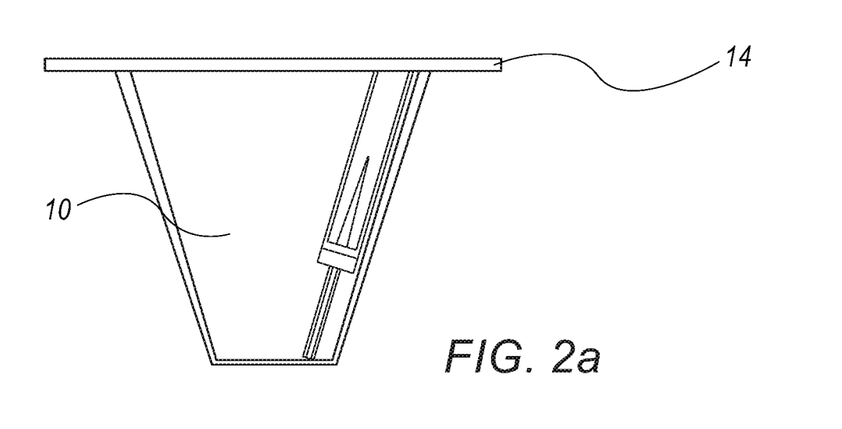
Figure 3:
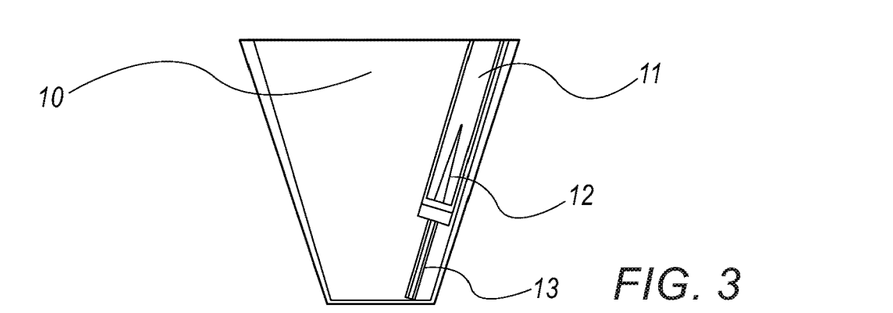
Figure 4:
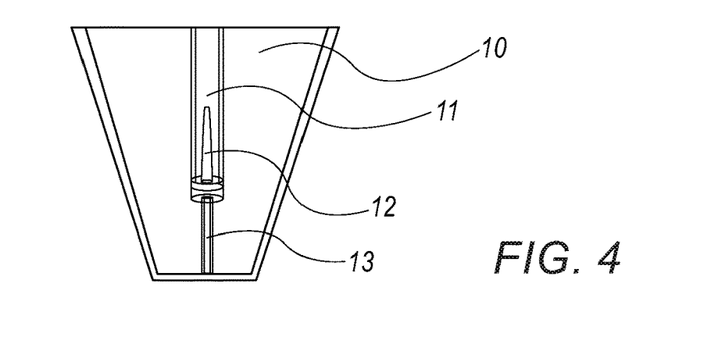

Reference is now made also to FIGS. 1a and 2a, which illustrate present top and side views of collector 10 and collector attachment extension 14 for fitting over a toilet seat, according to features of the present invention. The presented shape of collector attachment extension 14 is for explanatory purposes only, as extension 14 may be of any shape and not necessarily around all the perimeter of collector 10 upper part. Collector extension 14 may be placed on the toilet seat and may be attached either manually by using clips, bands or similar, or by utilizing a glue-like material to attach it to the toilet seat. Collector 10 may be detached from the toilet seat, by either a manual/powered trigger or due to a glue-like material that dissolves after a pre-defined time or a chemical reaction. Then, collector 10 may fall into the toilet or bin, by way of example.

Figure 9:
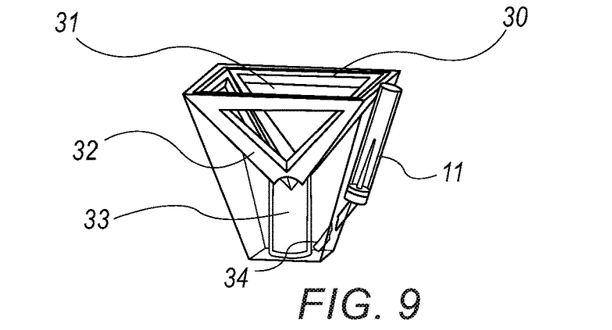
FIGS. 9, 10a/10b, 11 and 12 present respectively three dimensional isometric, two top views, front view and side view of an additional embodiment of a collector, according to features of the present invention.

Referring back to FIGS. 1-4, collector 10 has a main part and a pocket 11. Pocket 11 may be attached from either the inside as shown or outside as depicted in FIG. 9. Pocket 11 may be isolated from collector 10 and is open at its upper end to allow flow of air. A pipe 12 may extend through a narrow passage at the bottom of pocket 11 and may be connected to a feeding pipe 13 that extends from bottom of collector 10, through main part of collector 10, to bottom of pocket 10. Pipe 12 may be made of either a disposable, dissolving or a durable material. Pipe 12 may have sharp upper ends protected by a protrusion. During operation, urine is collected in collector 10, a sample container, e.g. an evacuated tube, may be inserted into pocket 11. A seal of the evacuated tube may be pierced by the sharp upper end of pipe 12 and may be filled with urine through the feeding part 12 of collector 10 and through feeding pipe 13. Alternatively, the sample container placed in pocket 11 may be filled by using a sub-pressure technique. Sub-pressure may be created by methods such as activating a simple piston (not shown) on collector 10. Once finished urinating, the user triggers the sample container to fill by applying light manual/powered force such as pushing, pulling or rotating. The air-evacuated sample container may be filled with urine once the top sharp end of pipe 12 penetrates the sample containers' seal at bottom of pocket 11 or following a piston activation on the sample container in pocket 11. Due to sub-pressure, the sample container in pocket 11 may be filled up to maximum volume capacity unless there isn't enough urine in the collector. The user obtains a clean, dry and sealed container, filled with the desired urine sample.

Reference is now also may to FIGS. 5-8 which depict respectively three dimensional isometric, top, front, and side views of a collector 20 of a second embodiment that together with the smart receptacle described below, is designed to provide a urine sample of a long urine collection. In each urination during the long collection, the user may use collector 20 and obtain a sealed sample container, e.g. evacuated tube, which holds urine in a volume proportional to the urine volume given during that urination. To enable that, collector 20 includes a main part 20 as in collector 10 and a sleeve 21 which includes pocket 11. The main part 20 and sleeve 21 are filled with urine in volumes proportional to their sizes as detailed below. The sample container, e.g. evacuated tube in pocket 11 is filled with the urine in sleeve 21 which is transferred into the smart receptacle. Sleeve 21 may be filled by using methods such as the mechanism of connected vessels or by applying a fluid distribution technique at the upper end of the collector. To enable a distribution mechanism based on the principle of connected vessels, sleeve 21 has a small passage, a feeding entry 22 between sleeve 21 and the main part 20 of the collector. Therefore, the urine in both parts, main chamber of collector 20 and sleeve 21 reaches the same level. An exemplary alternative fluid distribution technique from the upper part of the collector 20, is activated through a horizontally balanced membrane (not shown) stretched over the upper part of collector 20. The urine that flows into collector 20, is slightly detained by the membrane which is designed to allow even fluid spreading. Therefore, the two parts of the collector 20, the main part and sleeve 21, hold urine in volumes proportional to their volume capacities. As a result of either technique, sleeve 21 holds urine in a volume proportional to the total urine volume that filled collector 20. All the urine volume collected in sleeve 21 is intended to be transferred to the sample container placed in pocket 11. The dimensions of collector 20 and sleeve 21 are configured to allow collecting urine samples of both small and big amounts, as well as meeting the maximum volume capacity of the container (a tube or similar) placed in pocket 11.

As sub-pressure techniques may be used to fill the sample container in pocket 11 with the urine in sleeve 21, the feeding passage 22 is closed before filling. A plug may be created by a material that dissolves within a predefined time and seals passage 22 or by a seal that is already included in collector 20 and is triggered to block passage 22 by either time, manual/powered force or a chemical reaction with fluid (such as water, urine). An example to trigger by force is the action of pushing the sample container, e.g. evacuated tube in pocket 11 downwards that would first trigger the plug to close feeding passage 22.

Once feeding passage 22 is closed and a sub-pressure technique is used to fill the sample container placed in pocket 11, all the urine held in sleeve 21 is collected. The small collector holding urine in a volume proportional to the urine given at a specific urination may be emptied into the smart receptacle. As all dimensions are known, the volume in the sample container indicates by simple calculations based on proportional volumes and minimal fluid loss, the total volume of the urine that filled the collector. This may be done assisted by hardware and/or software included with the smart receptacle.

Figure 10A:
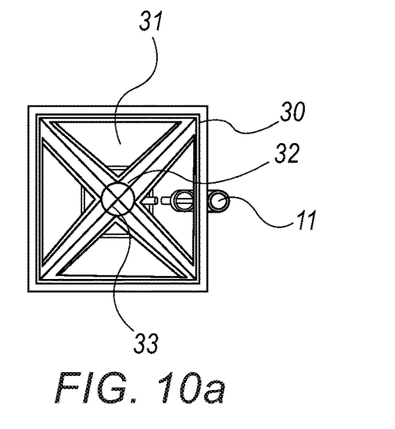
Figure 10B:
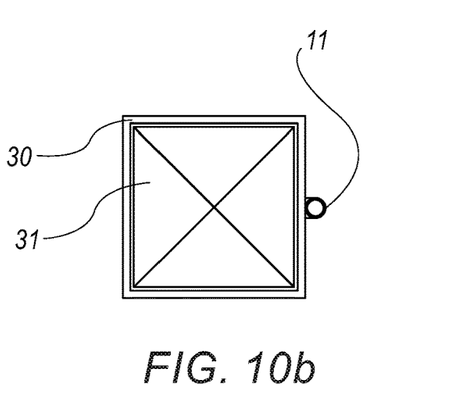
Figure 11:
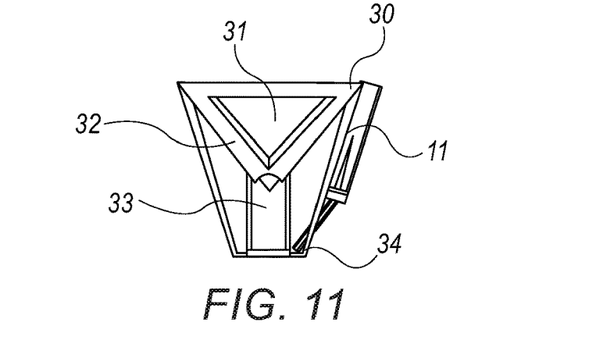
Figure 12:
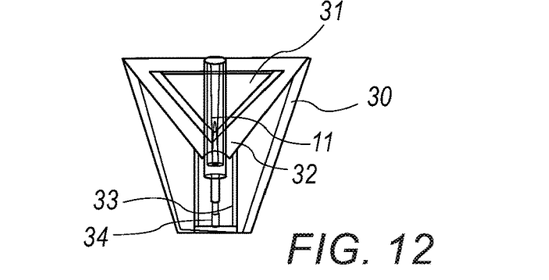

Reference is now also made to FIGS. 9, 10*a*/10*b*, 11 and 12 which illustrate respectively three dimensional view, top views, front view and side view of collector 30, directed to collect a sample for urine culture tests. Collector 30 separates between initial urine flow and subsequent urine flow and provides a urine sample of only the latter. Pocket 11 is depicted as attached to collector 30 from the outside (but can also be attached from inside). In exemplary embodiments, collector 30 upper perimeter is attached to and covered by container 31. Container 31 is intended to collect the initial urine, as depicted in FIG. 10*b*. Container 31 is made of a material affected by weight and its bottom end is placed in pipe 33 as depicted in FIG. 9. For explanatory purposes pipe 33 is shown in the middle of collector 30 however pipe 33 may be positioned closer to collector 30 walls. The urine weight causes container 31 to sink into pipe 33. At a pre-defined weight, the pressure may cause container 31 upper edge to tear in a controlled manner, assuring that the initial urine flows only into container 31 and pipe 33 and not into any other part of container 30. A possible tearing technique is applied by a thread that runs along the attachment of collector 30 and container 31. The thread lower end lies at the bottom of container 31. The urine weight causes container 31 to sink into pipe 33 and creates a pulling force on the thread resulting in detaching container 31 from collector 30 and continue its sinking into pipe 33. Pipe 33 bottom may be closed or open to remove the initial urine flow. Pipe 33 dimensions and materials prevent urine overflow or any other cause (such as diffusion) that could result in a mixture between the initial urine and the rest. Pipe 33 may be fastened to collector 30, for example, by strips 32 that are revealed after the sinking of container 31 into pipe 33. The rest of the urine, subsequent portion of urine after the initial flow, flows into collector 30. Pocket 11 and the sample container, e.g. evacuated tube, may be fed through a feeding entry 34. Therefore, the sample container may be filled with urine outward to pipe 33 that is neither contaminated by the initial urine flow nor by urine that flowed over parts that might have been contaminated by the initial urine.

Reference is now made to FIGS. 13-16 illustrating respectively three dimensional view, top view, front view and side view of a smart receptacle 40, which may be configured for measuring and/or reporting the urine volume collected during a long collection and provide a urine sample of the collection. Smart receptacle 40 is directed to collect urine samples over long collections, store them, provide a urine sample of the long collection and/or run immediate diagnostics on urine samples. A urine sample container containing a urine sample during a long collection may be inserted into a feeding socket 41 and urine content therefrom is emptied into chamber 44. After each urination during a long collection, the user empties sample container, e.g. tube filled with urine, by inserting it in feeding socket 41 of smart receptacle 40.

A second insertion socket 45 is shown for final collection of a combined urine sample from the multiple samples during the long collection by inserting an empty sub-pressure activated sample container to transfer urine sample from chamber 44. In some embodiments the functions of filling chamber 44 and sampling from chamber 44 may be combined using a single socket 41 and 45.

Insertion of the sample container into socket 41, may trigger by manual/powered force an action of seal 42. Seal 42 may include a mechanism for extracting or letting urine flow from the sample container and a valve that opens to let the urine sample flow from the sample container, through pipe 43, and fill smart receptacle chamber 44. Once completed, a manual/powered force may trigger seal 42 to close and eject the empty sample container.

In order to extract the urine from the sample container, seal 42 may have a sharp part that penetrates the sample containers' seal. As this action is repetitive for long collections, and in order not to contaminate the urine collection, the sharp part of seal 42 may be replaced with each insertion of a sample container.

After each event of a sealed sample container emptying into receptacle chamber 44, a change in urine volume inside chamber 44 may be detected by either sensors or by image capturing of the smart receptacle (having a transparent front). This data and additional data such as time, user ID, etc. may be transmitted to a relevant monitoring unit (healthcare, enforcement, etc.) and user who may receive personal guidance.

Upon completion of the long urine collection and before extracting a urine sample of the long collection, urine in chamber 44 may be mixed. The user may gently shake receptacle 40 or insert into chamber 44 a mixing element for manual or powered mixing.

A user may insert a sub pressure activated sample container into smart receptacle socket 45 and fill the sample container through a sharp ended pipe 46 and through the feeding pipe 47 with a urine sample that includes all the urine samples collected in chamber 44 during the long urine collection. The user may provide the filled sample container to the clinic for further diagnostics tests or if requested, provides the clinic with smart receptacle 40.

Reference is now also made to FIGS. 17 to 20 which illustrate respectively three dimensional view, top view, front view and side view of a smart receptacle 50, another exemplary embodiment of the present invention configured for immediate diagnostics of the urine stored in the sample container. Smart receptacle 50 may include a dipstick drawer 51 into which a dipstick may be inserted through a dipstick insertion socket 52 which is otherwise sealed to avoid spills. Upon design considerations for esthetic dipstick insertion and removal, the dipstick might be placed on a leading slide surface or in a box that would be inserted through insertion socket 52. In smart receptacle 50, as in receptacle 40, the sealed sample container may be inserted in feeding socket 41 of receptacle 50 and triggers by manual/powered force the action of special seal 53, to extract (or let flow) the urine from the sealed sample container and stream it through pipe 54 to fill the dipstick drawer 51. Once completed, seal 53 is triggered to close and eject the empty sample container.

In order to extract the urine from the sample container, seal 53 has a sharp part that penetrates the sample containers seal. For a re-usable smart receptacle 50, and in order not to contaminate the urine test, the sharp part of seal 53 may be replaced with each insertion of the sample container.

Reference is now made to FIGS. 20-1, 20-2, 20-3 and 20-4 which illustrate respectively a three dimensional view, top view, front view and side view of a dipstick drawer 51. Dipstick 57 (or a slide, box or the like holding and leading the dipstick into the dipstick drawer 51) may be placed horizontally or vertically in drawer 51, and dipstick 51 may be immersed through pipes of various sizes, diffusion materials or similar.

To emulate the immersion of dipstick 57 in fluid, the urine in dipstick drawer 51 may be held for a time to immerse dipstick 57. This may be done by streaming the fluid at a suitable predefined pace, for example through detained diffusion using applicable materials. Then, the urine flows to the bottom of drawer 51 to remove excess urine from dipstick 57. Additional time may be allowed for dipstick 57 chemical reactions to occur and reflect a change of color. The urine effect on the dipstick may be measured by sensors or by image capture of smart receptacle 50 (having a transparent face). This data and additional such as time, user ID, etc. is transmitted to both the relevant monitoring unit (healthcare, enforcement, etc.) and user who may receive personal guidance.

Figure 21:
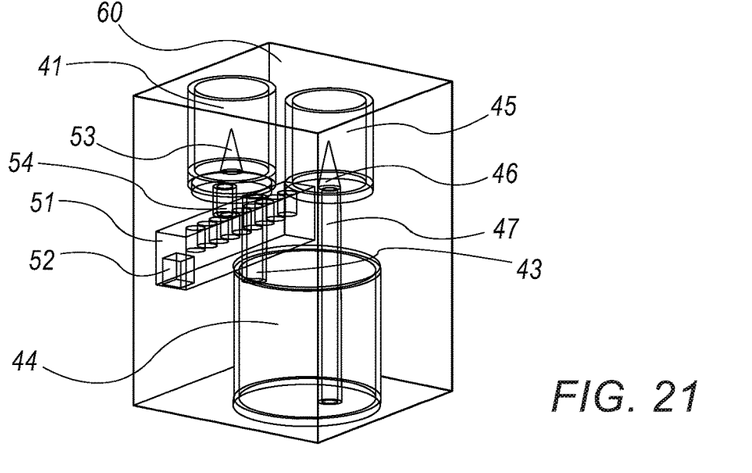
FIGS. 21 to 24 illustrate respectively a three dimensional isometric view, top view, front view and side view of another embodiment of the smart receptacle, according to features of the present invention.
Figure 22:
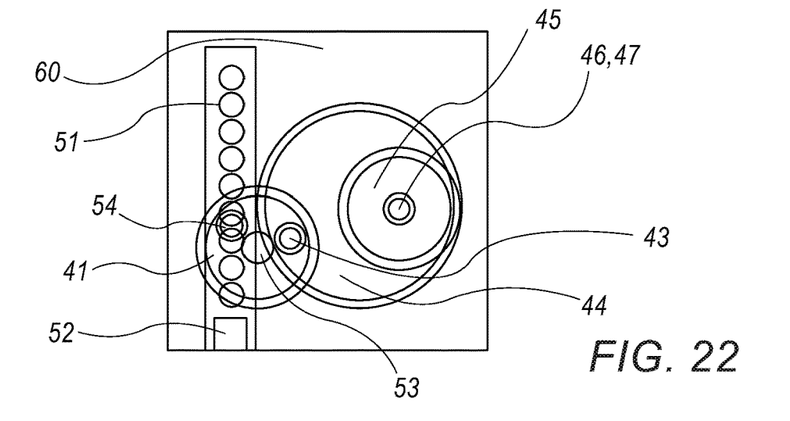
Figure 23:
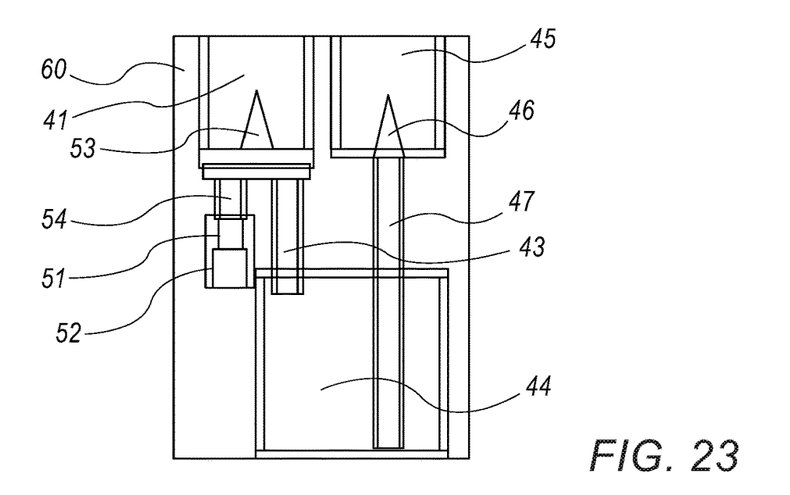
Figure 24:
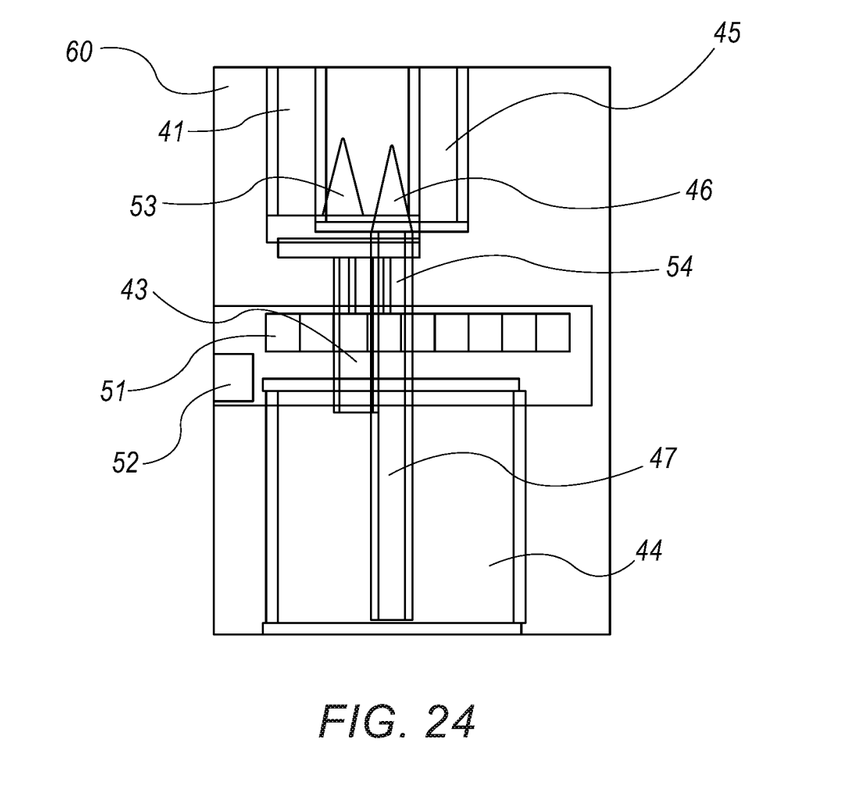

FIG. 21., FIG. 22., FIG. 23. and FIG. 24. illustrate another exemplary embodiment of smart receptacle 60, top view, front view and side view. Smart receptacle 60 is aimed to collect urine samples of long urine collections and/or run immediate diagnostics.

Figure 25:
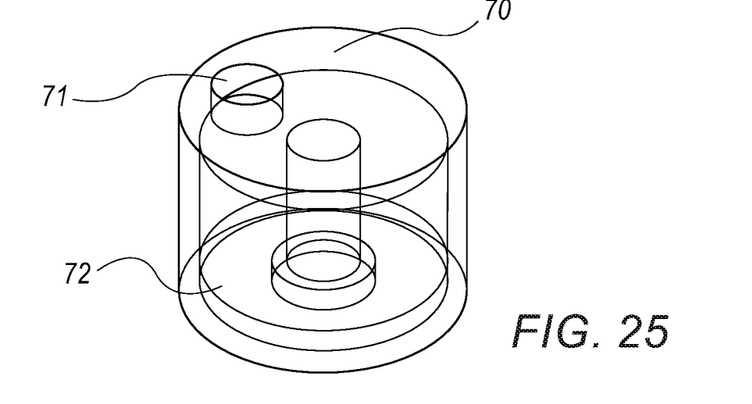
FIGS. 25 to 28 illustrate respectively a three dimensional isometric view, top view, front view and side view of another embodiment of the smart receptacle, according to features of the present invention.
Figure 26:
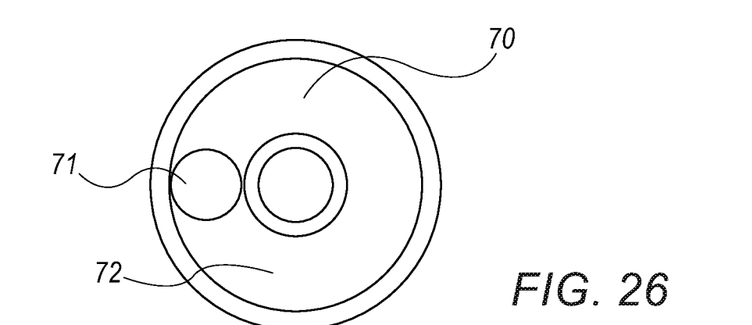
Figure 27:
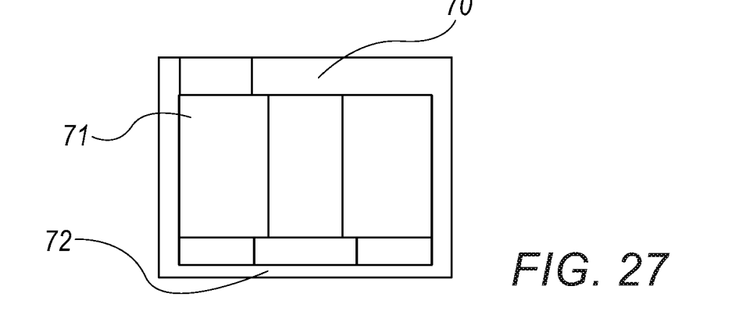
Figure 28:
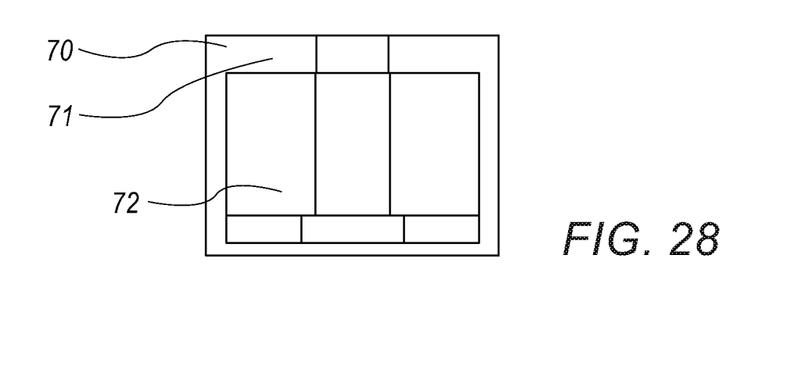
Figure 201:
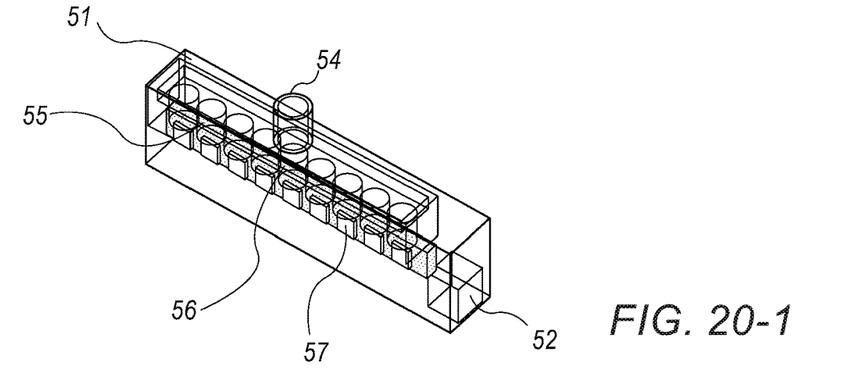
Figure 202:
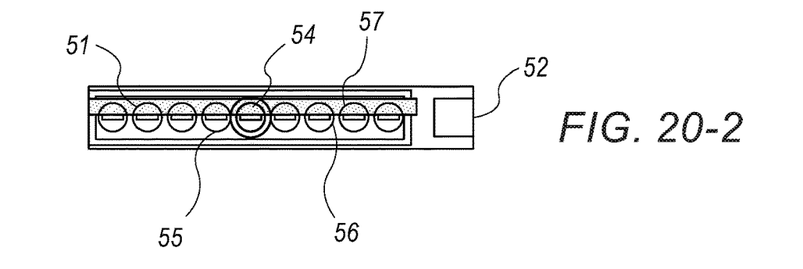
Figure 203:
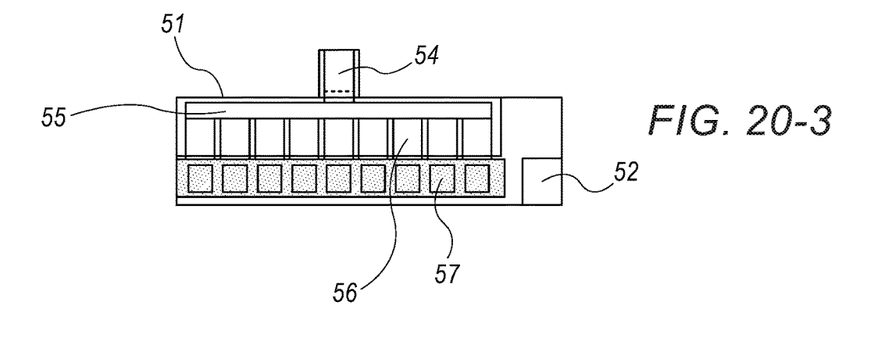
Figure 204:
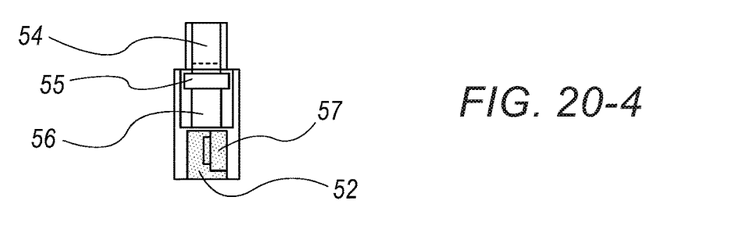

FIG. 25., FIG. 26., FIG. 27. and FIG. 28. illustrate respectively a three dimensional isometric view, top view, front view and side view of smart receptacle 70, according to features of the present invention. Smart receptacle 70 is aimed to collect the sample containers (tubes or similar) holding the urine samples collected throughout long urine collections, in order toc test the variations is urine substances during the long collection time period.

Unlike the other embodiments, smart receptacle 70 doesn't store together the content of all the sample containers as its purpose is to test the content of each urination sample throughout several hours. Therefore, it collects and stores the sample containers themselves. Each sample container gains an identification mark to set their order (which could be a barcode, a QR or else). The sample containers are opened in a laboratory, to test and track variations in the urine substances during the collection hours. Naturally the samples can also be tested by the immediate diagnostics' smart receptacle 50. Smart receptacle 70 is shown as a round receptacle, but it could be of any shape.

The smart receptacle entry socket 71 is used to insert the sample container (a tube or similar). Once the tube (or a similar container) is inserted, it gains an identification mark (unless it already has an identification mark) to set its order. Each event of a tube insertion triggers the former tubes (or similar) to move a notch in 72, the area in which the containers are stored. The mechanism for marking each container and the mechanism for advancing the containers in 72 will either be commercial existing products/former inventions or new developments that will be described separately. For example, the tubes (or similar containers) could be loaded into 72 in a mechanism similar to loading cartridges into a magazine.

Space 72 size is designed to allow storing of all the containers used throughout long collections. The tubes (or similar containers) order can be detected by sensors or by photo capturing of the smart receptacle that matches the identification mark of each container to its order. This data and additional such as time, user ID, volume, etc. is transmitted to both the relevant monitoring unit and user. Upon completion of the urine collection, the smart receptacle containing the test tubes (or similar containers), is provided to clinic or the like to analyze the urine substances' variations. The substances analyze results together with the containers order that is already set, allows presenting graphs of variations in the urine content.

Figure 5:
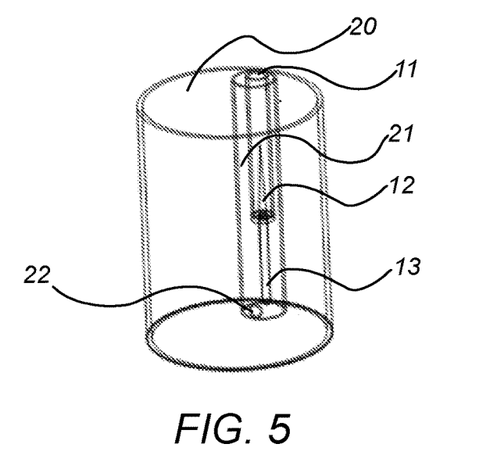
FIGS. 5 to 8 present respectively three dimensional isometric, top view, front view and side view of a second embodiment of a collector, according to features of the present invention.
Figure 6:
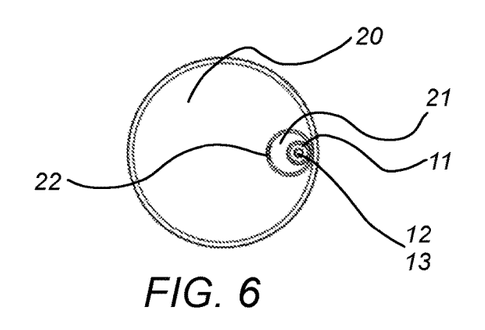
Figure 7:
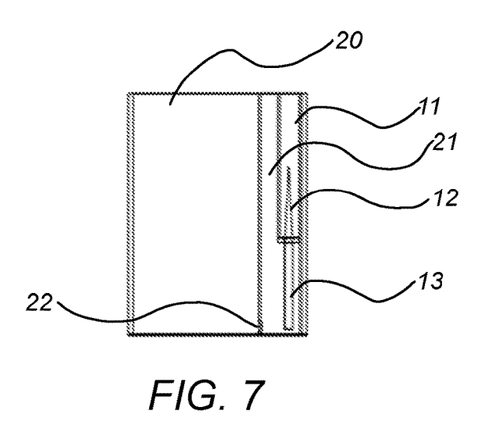
Figure 8:
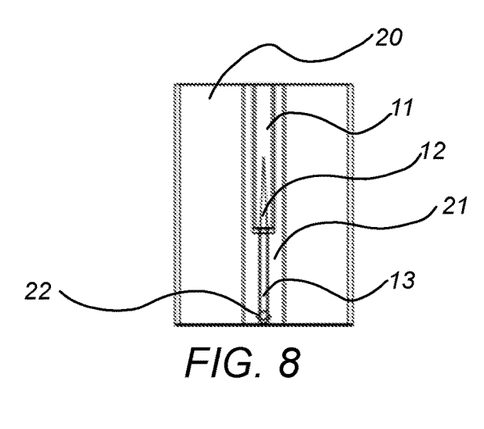

Embodiments of the collector as presented in FIG. 1, FIG. 5, and FIG. 9 may either be 'standalone', modular or combined into one.

Figure 13:
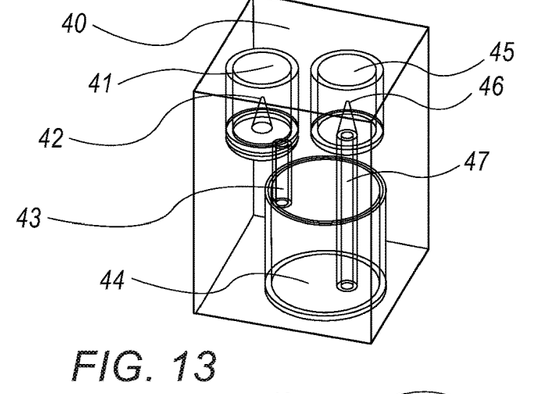
FIGS. 13 to 16 illustrate respectively three dimensional isometric, top view, front view and side views of an embodiment of a smart receptacle, according to features of the present invention.
Figure 14:
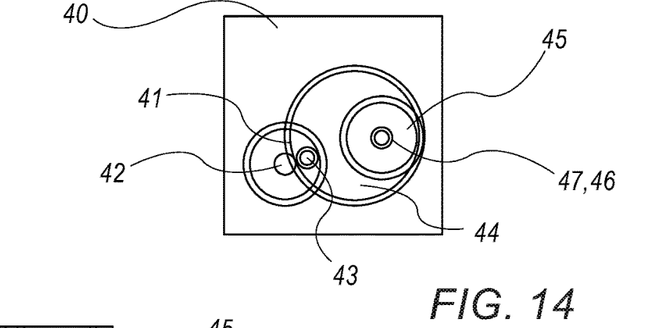
Figure 15:
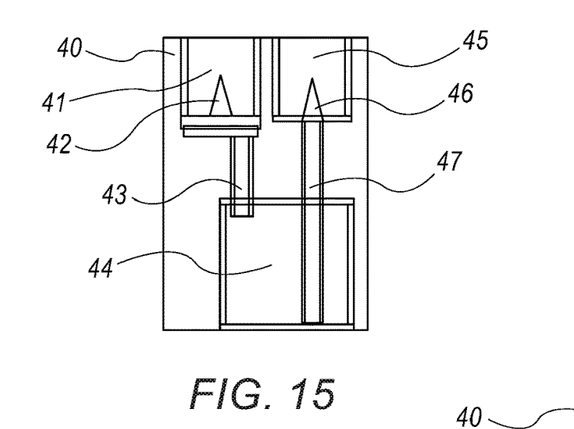
Figure 16:
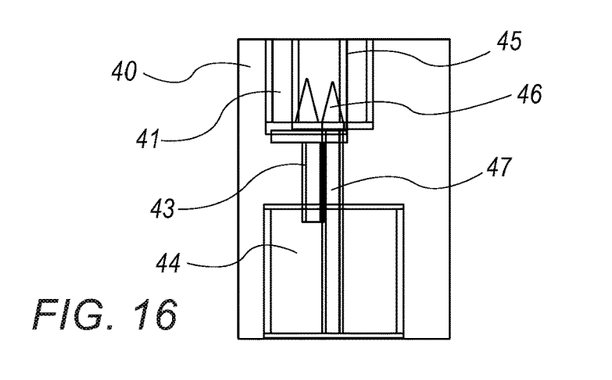
Figure 17:
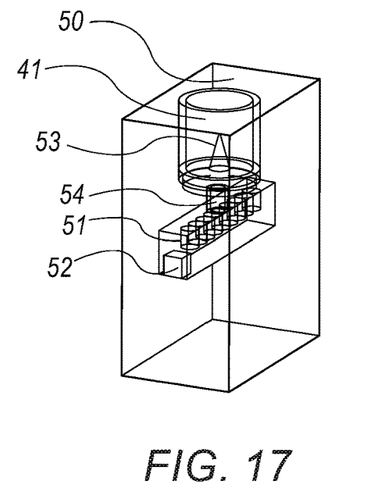
FIGS. 17 to 20 present respectively three dimensional isometric view, top view, front view and side view of a smart receptacle, according to features of the present invention.
Figure 18:
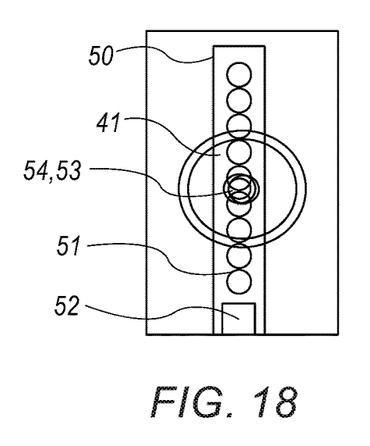
Figure 19:
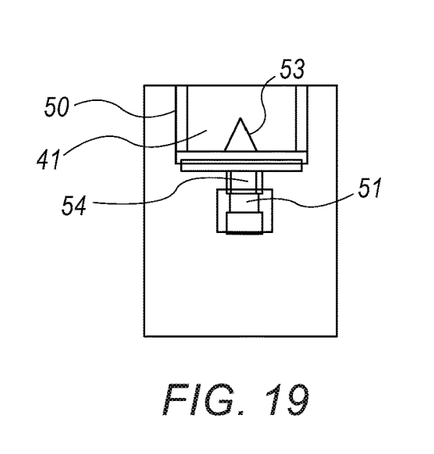
Figure 20:
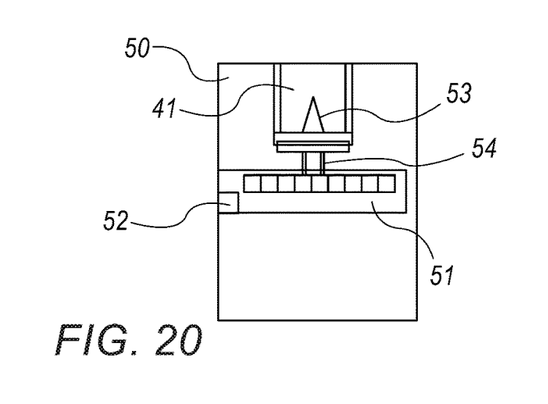

Embodiments of the smart receptacle as presented in FIG. 13 and FIG. 17 may be standalone, modular or combined as shown in FIG. 21, but not only. FIG. 25 depicts an additional type of a smart receptacle embodiment.

The present application is gender neutral and personal pronouns 'he' and 'she' are used herein interchangeably.

The terms "toilet" and "bin" are used herein interchangeably and refer to any of a flush toilet connected to sewage drain; or, a portable commode, a toilet chair, a portable toilet, and/or a bedside commode which are not permanently connected to a sewage drain.

The terms "sealed container" and "sample container" are used herein interchangeably.

The term "parameter" as used herein in the context of accumulated urine may refer to urine level, volume, weight, an amount of one or more substances included in the accumulated urine.

Although selected features of the present invention have been shown and described, it is to be understood the present invention is not limited to the described features.

The terminology used herein is for the purpose of describing particular embodiments only and is not intended to be limiting of the disclosure. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. Unless otherwise defined, all terms (including technical and scientific terms) used herein have the same meaning as commonly understood by one having ordinary skill in the art to which this disclosure belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the disclosure, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the disclosure and the claims.

New collector and smart receptacle embodiments for collecting urine samples and related data are discussed herein. For purposes of explanation, numerous specific details are set forth in order to provide a thorough understanding of the present disclosure. It will be evident, however, to one skilled in the art that the present disclosure may be practiced without these specific details.

The present disclosure is to be considered as an exemplification of the disclosure and is not intended to limit the disclosure to the specific embodiments illustrated by the figures or description below.

While the invention has been described with respect to a limited number of embodiments, it will be appreciated that many variations, modifications and other applications of the invention may be made.

The claimed invention is:

1. A method comprising:
   providing a collector with an extension lip;
   placing the collector inside a toilet with the extension lip placed on a toilet seat disposed on top of the toilet, wherein the collector includes a hollow sleeve disposed inside or outside the collector, wherein urine disposed inside the collector and inside the sleeve attain the same fluid level responsive to a fluid passage between the collector and the sleeve at the bottom of the collector;
   upon collecting a urine sample, closing the fluid passage between the collector and the sleeve, and extracting a volume of urine contained in the sleeve, wherein the volume of urine extracted from the sleeve is proportional to the urine collected inside the collector with a known proportionality constant.

2. The method, according to claim 1, further comprising:
   providing a pocket configured to receive a sealed container with a seal;
   inserting the sealed container into the pocket thereby penetrating the seal by the pocket prior to extracting the urine sample into the sealed container.

3. The method, according to claim 1, wherein the collector includes a plurality of compartments, the method further comprising:
   separating an initial urine flow from a subsequent urine flow;
   said extracting the sample of urine only from a compartment including the subsequent urine flow.

4. The method, according to claim 1, further comprising:
   repeating said collecting the urine sample and said extracting the volume of urine contained in the sleeve a plurality of instances during a previously determined time period;
   for all said instances, transferring a volume of urine contained in the sleeve to a receptacle, wherein urine accumulated in the receptacle is proportional to a total volume of urine collected during the previously determined time period with the known proportionality constant.

5. The method, according to claim 4, further comprising:
   providing a sensor in the receptacle;
   measuring by the sensor a parameter of the urine accumulated in the receptacle.

6. The method, according to claim 4, further comprising:
   capturing an image of the urine through a transparent face of the receptacle.

7. A system comprising:
   a collector with an extension lip, wherein the collector is configured to fit inside a toilet with the extension lip placed on a toilet seat disposed on top of the toilet;
   a mechanism configured for extracting a sample of urine from inside the collector; wherein the collector includes a hollow sleeve disposed inside or outside the collector, wherein urine disposed inside the collector and inside the sleeve attain the same fluid level responsive to a fluid passage between the collector and the sleeve at the bottom of the collector,
   a mechanism configured for closing the fluid passage between the collector and the sleeve upon collecting the sample of urine;
   wherein the volume of urine extracted from the sleeve is proportional to the urine collected inside the collector with a known proportionality constant.

8. The system, according to claim 7, further comprising:
   a pocket configured to receive a sealed container with a seal;
   wherein the sealed container is insertable into the pocket to penetrate the seal by the pocket prior to said extracting the sample of urine into the sealed container.

9. A system comprising:
   a collector with an extension lip, wherein the collector is configured to fit inside a toilet with the extension lip placed on a toilet seat disposed on top of the toilet;
   a mechanism configured for extracting a sample of urine from inside the collector, wherein the collector includes a plurality of compartments:
   a mechanism configured to separate initial urine flow into a first compartment from subsequent urine flow into a second compartment, wherein weight of urine of the initial urine flow enables at least a portion of the first compartment to detach and sink into a third compartment thereby enabling the second compartment to receive only the subsequent urine flow.

10. The system, according to claim 7, further comprising:
    a receptacle, wherein a plurality of urine samples extractable from the sleeve are transferable to the receptacle; wherein urine accumulated in the receptacle is proportional to a total volume of urine collected during a previously determined time period with the known proportionality constant.

11. The system, according to claim 10, further comprising:
    a sensor configured to measure a parameter of the urine accumulated in the receptacle.

12. The system, according to claim 10, further comprising:
    a transparent face of the receptacle, wherein an image of the urine is captured through the transparent face of the receptacle.

* * * * *